ns. Filed: May 11, 1970

United States Patent [19]
Russell et al.

[11] 3,960,954
[45] June 1, 1976

[54] PROCESS FOR PREPARING OXIMES AND HYDROXYLAMINES

[75] Inventors: Joseph Lee Russell, Ridgewood; John Kollar, Wyckoff, both of N.J.

[73] Assignee: Halcon International, Inc., New York, N.Y.

[22] Filed: May 11, 1970

[21] Appl. No.: 36,378

Related U.S. Application Data

[63] Continuation-in-part of Ser. No. 732,079, May 27, 1968, abandoned, which is a continuation-in-part of Ser. No. 434,089, Feb. 19, 1965, abandoned, which is a continuation-in-part of Ser. No. 355,485, March 27, 1964, abandoned.

[52] U.S. Cl. .................... 260/566 A; 260/563 R; 260/584 R; 260/570.5 R
[51] Int. Cl. .................................... C07c 119/00
[58] Field of Search ............... 260/566 A, 570.5 R, 260/584 R, 563 R

[56] References Cited
UNITED STATES PATENTS

| 2,706,204 | 4/1955 | Kahr | 260/566 |
| 2,795,611 | 6/1957 | List | 260/566 |

FOREIGN PATENTS OR APPLICATIONS

| 6,511,461 | 8/1966 | Netherlands | 260/566 A |

*Primary Examiner*—James O. Thomas, Jr.
*Assistant Examiner*—Alan Siegel
*Attorney, Agent, or Firm*—William C. Long; David Dick; Riggs T. Stewart

[57] ABSTRACT

Oximes and hydroxylamines are prepared by reacting a primary amine, the amino group of which is attached to a primary or secondary carbon atom, with an organic hydroperoxide in the presence of a catalytic amount of a compound of Ti, V, Cr, Se, Zr, Nb, Mo, Te, Ta, W, Re, or U.

4 Claims, No Drawings

PROCESS FOR PREPARING OXIMES AND HYDROXYLAMINES

RELATED APPLICATION

This application is a continuation-in-part of application Serial No. 732,079 filed May 27, 1968, now abandoned, which is a continuation-in-part of Serial No. 434,089 filed February 19, 1965 now abandoned, which is a continuation-in-part of Serial No. 355,485 filed March 27, 1964 now abandoned.

BACKGROUND OF THE INVENTION

Ketoximes and other oxygenated amine compounds are increasingly important intermediates for chemical manufacture. The art has appreciated the desirability of being able to produce ketoximes and hydroxylamines from the corresponding amines, and a suggested procedure involves using hydrogen peroxide in an aqueous system. Although this system may give little or no by-products, a major problem is the relatively high cost of this oxidizing agent. Organic hydroperoxides have not been regarded as feasible for such a process and they might be expected to form troublesome by-products. The art is confronted by the problem of providing processes for producing hydroxylamines and oximes from corresponding primary amines in a convenient and economic manner.

This invention provides an answer to the problem of producing oximes or hydroxylamines in an economical fashion while conserving or improving essential raw material values.

The discoveries associated with the invention and relating to the solution of the above problems, and other objects achieved in accordance with the invention as set forth herein include the provision of:

a process for preparing an oxygenated amine such as an oxime or a hydroxylamine from the corresponding primary amine; the amine group being attached to a primary or secondary carbon atom, which process comprises treating the amine with a combination of (1) a dissolved metal catalyst of the group consisting of peracid forming or hydroxylation catalysts (i.e. compounds of Ti, V, Cr, Se, Zr, Nb, Mo, Te, Ta, W, Re, and U) and (2) an organic hydroperoxide as the essential oxidizing agent; (the amount of oxidizing agent being in the range of 0.01 to 10 mols per mol of the amine, and the amount of metal being in the range of 0.00001 to 0.1 mols per mol of the hydroperoxide, preferably);

such a process wherein the temperature is in the range of about −10° to +175°C.;

such a process wherein cyclohexanone oxime is prepared using cyclohexyl hydroperoxide;

such a process wherein cyclohexanone oxime is prepared using cumene hydroperoxide, or a hydroxy-hydroperoxide;

such a process wherein the catalyst is a molybdenum compound;

such a process wherein the catalyst is a vanadium compound;

such a process wherein the amine group is attached to a secondary carbon atom of a cycloalkyl group having 4 to 16 carbon atoms;

such a process wherein the hydroperoxide is prepared by reacting gaseous oxygen with ethylbenzene in the presence of an oxidation initiator, the amine has 1 to 20 carbon atoms, and by-product alpha-phenylethanol is recovered;

such a process wherein the unreacted ethylbenzene is recycled to the hydroperoxide preparation step;

such a process wherein the alpha-phenylethanol is dehydrated to form styrene;

such a process wherein the dehydration step is in the vapor phase over titania catalyst at a temperature in the range of 180° to 280° C.

such a process wherein a catalytic amount of molybdenum disulfide is the catalyst;

such a process wherein the alpha-phenylethanol is dehydrogenated to form acetophenone, and the latter is recovered;

such a process wherein the alpha-phenylethanol is hydrogenated to ethylbenzene, and the latter is used forming its hydroperoxide;

such a process wherein the hydroperoxide is prepared by reacting gaseous oxygen with cumene in the presence of an oxidation initiator, the amine has 1 to 20 carbon atoms, and by-product cumyl alcohol is recovered;

such a process wherein a catalytic amount of a molybdenum salt of a carboxylic acid is the catalyst;

such a process wherein the cumyl alcohol is converted to cumene, and the latter is used to form its hydroperoxide;

such a process wherein the cumyl alcohol is converted to alpha-methyl styrene;

such a process wherein n-hexylaldoxime is prepared from n-hexylamine;

such a process wherein a hydroxylamine is prepared from the corresponding amine;

such a process wherein cyclohexylhydroxylamine is prepared;

and other objects which will be apparent as details or embodiments of the invention are set forth hereinafter.

DETAILED DESCRIPTION

In essence, the invention involves the finding that the hydroperoxides which are readily formed by the oxidation of the above mentioned hydrocarbons are unexpectedly suitable for causing the oxidation of a primary amine, the amine group of which is attached to a carbon atom of the class consisting of primary and secondary carbon atoms, i.e., to form aldoximes or ketoximes respectively. Moreover, while the new process here described consists of a number of steps, it is not necessary to separate any of the reaction intermediates so that the series of reactions involved can be carried out in particularly expeditious fashion.

In the first step of the new process, the hydrocarbon is oxidized using atmospheric oxygen, e.g., cumene to cumene hydroperoxide. The oxidation of the hydrocarbon such as cumene can be carried out to conversions up to 40% with high selectivity. Aliphatic hydroperoxides are obtained at somewhat lower selectivity by oxygen oxidation. The resulting oxidation mixture contains the starting material as the hydroperoxide resulting from the oxidation. It also contains very minor amounts of by-products. Introduction of the primary amine into this mixture (or a concentrate thereof), either as a molybdenum or equivalent catalyst is being added or after catalyst addition is complete, leads to the corresponding oxime or hydroxylamine and, of course, to cumyl alcohol, if cumene hydroperoxide is used.

The mixture of reaction products obtained as above described also contains some acetophenone in addition to the alcohol. From this mixture the oxygenated amine is readily separated by distillation or other convenient method.

It may be desirable to introduce an inert solvent when the hydroperoxide, such as alpha-phenylethyl hydroperoxide or cumene hydroperoxide, concentration is greater than approximately 30–40%. The material chosen should be one which does not react with the peroxide oxygen or the oxygenated amine formed in the reaction. The solvent can be chosen from substances such as t-butyl alcohol, alpha-phenylethanol, cumyl alcohol, benzene, toluene, ethylbenzene, cumene and the like.

The secondary alcohols may be dehydrogenated (in known manner) to produce ketones, e.g., acetophenone (from alpha-phenylethanol) which is marketable. As an alternate course, the alcohols (secondary or tertiary) can readily be dehydrated in known manner and converted to styrene or substituted styrene or isobutene which are marketable. The former is readily purified in known manner by distillation under vacuum to a premium grade material. Also, the alcohol or olefin derived from it is readily converted in known manner to the starting hydrocarbon, which is recycled, and this results in a no by-product process. However, hydrogen is consumed therein.

In order to indicate more fully the nature of the present invention, the following examples of typical procedures are set forth in which parts and percents are expressed by weight, unless otherwise indicated, it being understood that these examples are presented as illustrative only and are not intended to limit the scope of the invention.

EXAMPLE 1 a mixture of t-butanol (10.1 grams), cyclohexylamine (2.0 grams) vanadium naphthenate in naphthenic acids, (containing 3.4% vanadium) (0.1 grams) and cumene hydroperoxide (4.9 grams), is prepared at room temperature and brought up to 80° C., and held there without agitation for two hours. The resulting mixture contains cyclohexanone oxime; the hydroperoxide conversion is about 62%. The oxime yield is 45% based on cumene hydroperoxide converted. Analysis may be in any convenient manner, e.g., gas chromatography.

The oxime is recovered in usual manner. Where the amine forms a complex with the oxime it is recovered as a solid, e.g., in an aqueous system. The oxime may be separated therefrom by distillation, extraction with cyclohexane, or equivalent methods.

EXAMPLE 2

The procedure of Example 1 is repeated except using cyclohexyl hydroperoxide (10.0 grams) as the oxidizing agent at room temperature for 24 hours and 0.10 grams of molybdenum naphthenate (containing 5% Mo.). The hydroperoxide is prepared in known manner by treating cyclohexane with air, followed by vacuum distillation of unreacted cyclohexane to give the material used (containing 2.28 millimols of hydroperoxide per gram). After the reaction the mixture contains the oxime. The hydroperoxide conversion is 90% and the oxime selectivity based on reacted hydroperoxide is 26%.

EXAMPLE 3

The procedure of Example 2 is repeated except using a temperature of 60° C. for 17 hours. The reaction mixture contains the oxime, the hydroperoxide conversion is 100% and the oxime selectivity based on reacted hydroperoxide is 45%.

EXAMPLE 4

The procedure of Example 2 is repeated using as the catalyst 0.1 gram of 3.4% vanadium in naphthenic acids. the hydroperoxide conversion is 100% and based thereon, the oxime selectivity is 55%.

EXAMPLE 5

The procedure of Example 4 is repeated except at 60° C. for 17 hours; the conversion is the same (100%) and the oxime selectivity is 60%. Cyclohexylhydroxylamine is also produced, at a selectivity of a few percent.

EXAMPLE 6

The procedure of Example 2 is repeated except using 10 grams of cyclohexylamine and reacting for 24 hours at room temperature. The conversion of peroxide is 93% and the selectivity to cyclohexylhydroxylamine is 63%.

EXAMPLE 7

The procedure of Example 6 is repeated except using (4.9 grams) cumene hydroperoxide and reacting at 60° C. for 6 hours, and similar results are obtained.

EXAMPLE 8

About 7.5 grams of 88% alpha-phenylethyl hydroperoxide, 7.5 grams of alpha-phenylethanol, 0.6 grams of molybdenum naphthenate (containing 2% Mo) and 16.0 grams of amine are reacted as in Example 5 and similar results are obtained.

EXAMPLE 9

The oxidation is conducted essentially as described in Example 8, except that the catalyst is 0.016 grams of permolybdic acid and similar results are obtained.

Good results are also obtained using molybdenum disulfide as the catalyst in such oxidation runs.

EXAMPLE 10

The procedure of Example 2 is repeated except with 10 grams of a solution of the hydroperoxide of p-ethyl toluene in ethyl toluene, 16.8 grams of the amine, and 0.03 grams of naphthenate containing 5% Mo; similar results are obtained.

EXAMPLE 11

Following Example 10 except using 5 grams of cumene hydroperoxide, 5 grams of cumyl alcohol, 0.2 grams of catalyst solution containing 3.4% vanadium as naphthenate, and 10 grams of the amine, similar results are obtained.

Following Example 10 except using n-hexylamine, the corresponding n-hexylaldoxime is prepared in good yields.

Tungsten carbonyl catalyst may be used in these examples in a similar manner.

EXAMPLE 12

The following runs demonstrate the outstanding results achieved with titanium catalysts.

In each case cyclohexylamine was reacted with cumene hydroperoxide for the indicated time at 92° C., the mol ratio of cyclohexylamine to cumene hydroperoxide being 2.1/1. Various titanium compounds were used as catalysts as indicated. The runs were all operated with removal of cumene and water vapors, condensation and return of cumene to the reaction after water separation. The following table shows the results obtained:

EXAMPLE 14

Example 1 is repeated using an equivalent molar amount of tantalum naphthenate and cyclohexanone oxime is produced in good yield.

EXAMPLE 15

Example 1 is repeated using an equivalent molar amount of niobium naphthenate and cyclohexamine oxime is produced in good yield.

TABLE 1

| Run No. | 1 | 2 | 3 | 4 | 5 | 6 | 7 |
|---|---|---|---|---|---|---|---|
| Charge, g. | | | | | | | |
| Cumene hydroperoxide | 15.0 | 15.0 | 15.0 | 15.0 | 15.0 | 15.0 | 15.1 |
| Cyclohexylamine | 18.0 | 18.0 | 18.0 | 18.0 | 18.0 | 18.0 | 18.8 |
| Benzene | 42.8 | 41.7 | 41.3 | 42.4 | 42.7 | 41.3 | 30.2 |
| Catalyst | A | B | C | D | E | A | F |
| Catalyst amount, millimols | 1.46 | 1.46 | 1.46 | 1.46 | 5.82 | 5.82 | 5.82 |
| WT. % Ti in catalyst | 14.1 | 4.5 | 3.5 | 7.8 | 14.1 | 14.1 | 2.5 |
| Moles cumene hydroperoxide per mol Ti | 57.8 | 57.8 | 57.8 | 57.8 | 14.3 | 14.3 | 14.3 |
| Reaction time, hours | 0.75 | 1.0 | 1.0 | 0.5 | 0.5 | 0.75 | 0.5 |
| Cumene hydroperoxide conversion, wt. % | 100 | 99 | 100 | 100 | 99 | 100 | 100 |
| Reaction mixture | | | | | | | |
| Wt. & cyclohexanone oxime | 5.86 | 5.3 | 3.8 | 5.3 | 5.0 | 6.06 | 2.7 |
| Wt. % cyclohexylamine | 17.8 | 17.7 | 17.0 | 17.7 | 17.1 | 17.8 | — |
| Selectivity to oxime | | | | | | | |
| % based on hydroperoxide | 90 | 81 | 58 | 81 | 77 | 93 | 42 |
| % based on amine | 89 | 74 | 51 | 74 | 67 | 92 | 72 |

A — Tetra n-butyl titanate
B — di n-butyl di(2,6 di-t-butyl p-cresyl) titanate
C — n-butyl trioleoyl titanate
D — tetra o-cresyl titanate
E — tetra t-butyl titanate
F — titanium naphthenate

EXAMPLE 13

Cyclohexanone oxime was prepared by the reaction of alpha phenyl ethyl hydroperoxide (ethylbenzene hydroperoxide) with cyclohexylamine in the presence of various titanium catalysts. In each run the reaction mixture was refluxed 20 minutes and rapidly quenched. The following table shows the reaction conditions and the results obtained:

EXAMPLE 16

Example 1 is repeated using an equivalent molar amount of rhenium heptoxide and cyclohexamine oxime is produced in good yield.

EXAMPLE 17

Example 1 is repeated using an equivalent molar

TABLE 2

| Run No | 8 | 9 | 10 | 11 | 12 |
|---|---|---|---|---|---|
| Charge, g. | | | | | |
| EBHP | 10.0* | 10.0* | 10.0* | 10.0* | 10.0* |
| Cyclohexylamine | 5.7 | 5.7 | 5.7 | 5.7 | 5.7 |
| Benzene. | 18.3 | 17.5 | 18.2 | 18.4 | 18.0 |
| Catalyst | A | B | F | D | G |
| Catalyst amount, g. | 0.17 | 0.53 | 0.94 | 0.30 | 0.09 |
| Moles EBHP per mol Ti | 58.9 | 58.9 | 58.9 | 58.9 | 58.9 |
| Temperature, °C. | 98 | 98 | 98 | 92 | 90 |
| EBHP Conversion, % | 100 | 100 | 100 | 100 | 100 |
| Reaction mixture | | | | | |
| Wt. % cyclohexanone oxime | 4.0 | 4.2 | 3.7 | 4.1 | 3.2 |
| Wt. % cyclohexylamine | 12.4 | 12.4 | 12.3 | 12.3 | 12.6 |
| Selectivity to oxime | | | | | |
| % based on EBHP | 84 | 88 | 78 | 86 | 70 |
| % based on amine | 82 | 86 | 74 | 81 | 68 |

*39.6 wt % ethylbenzene hydroperoxide in ethylbenzene
**40.3 Wt % ethylbenzene hydroperoxide in ethylbenzene A, B, D, and F are as described in Example 12 and G is titanium tetrachloride.

In each of these runs the hydroperoxide was substantially quantitatively converted in this alpha phenol ethanol. In each instance, this latter material was separated by distillation and vaporizer and then dehydrated at 230° C. and about atmospheric pressure over titania pellets to produce styrene in about 80% yield.

amount of selenium naphthenate and cyclohexamine oxime is produced in good yield.

These are indeed surprising results and of great commercial value in view of the relatively low cost of the oxidizing agent, and the convenience of the operation. Also, this agent does not undergo undesirable decomposition as does hydrogen peroxide.

The oxidation of alkyl, cycloalkyl or aralkyl hydrocarbon such as ethylbenzene or cumene may be carried out in known manner so as to favor forming substantially all hydroperoxide. If there is a suitable market, the sideproduct alcohol which may be formed may be recovered and sold. Alternatively, the alcohol may be dehydrated to form a styrene or in the case of secondary alcohols, dehydrogenated in known manner to produce acetophenone, both of which are valuable materials. Also, it may be hydrogenated back to the starting hydrocarbon.

In the case of alpha-phenylethanol (formed from the hydroperoxide on about a mol for mol basis), it is converted in 80% or better yield to styrene by vapor phase dehydration at 200° to 250° C. over titania pellets or the like oxide catalyst at atmospheric pressure. Other catalysts include silica or alumina. The styrene is distilled to high purity commercial material.

In an alternate, alpha-phenylethanol is dehydrogenated to acetophenone, at 200° to 300° C. in the presence of copper catalyst and the ketone is recovered and purified by distillation, in known manner.

In another alternate, the alcohol is converted in known manner to the starting hydrocarbon, which is recycled.

Isobutane is reacted with oxygen to produce tertiary butyl hydroperoxide, which is reacted with the amine to produce the oxygenated amine, and t-butanol. The latter may be used to prepare i-butene, or may be marketed, or may be converted to isobutane.

In the first step, isobutane is reacted in the vapor phase with air and hydrogen bromide catalyst at a pressure of about 1 atmosphere and a temperature of 160° C. using 2 mols oxygen per mol isobutane and a space velocity of about 1000 volumes of gaseous mixture/vol. of reactor/hour. The effluent gaseous mixture is cooled to about 30° C. and condensed, and tertiary butyl hydroperoxide is recovered from the condensate by distillation at about 50° C., in known manner. The conversion of isobutane is 30%, and the selectivity of isobutane reacted to tertiary butyl hydroperoxide is 65%. Unreacted isobutane is recovered and recycled.

Alternatively, the isobutane is oxidized by passing oxygen through 800 grams of liquid isobutane, to which 5 grams of di-tertiary-butyl peroxide and 1 gram of iron naphthenate had been added, in a stainless steel reactor at a temperature of 110° C. and 600 p.s.i.g. The operation is continued until 25% of the isobutane is converted.

Analysis of the resulting reaction products (isobutane-free) shows a tertiary-butyl hydroperoxide equivalent per 100 grams of about 1.0.

The oxidation of isobutane may be carried out so as to favor forming substantially all tertiary butyl hydroperoxide. However, it is also possible to obtain a mixture of tertiary butyl hydroperoxide and tertiary butyl alcohol, and these may be separated by distillation. If there is a suitable market, excess t-butanol may be sold. Since, tertiary butyl alcohol is a desirable component of the system used to oxidize the amine with the hydroperoxide, separation of t-butanol from the hydroperoxide is not required for this invention. The fact that such separation need not be carried out is, of course, economically advantageous. In addition to the above techniques, any of the known methods for reacting isobutane with molecular oxygen to form tertiary butyl hydroperoxide can be used.

In the second step, the hydroperoxide is converted to tertiary butyl alcohol, on substantially a mol for mol basis. The tertiary butyl alcohol may be dehydrated to isobutylene thermally or over a suitable catalyst such as activated alumina or silica-alumina at a temperature in the range of 150° to 500° C. in known manner with substantially 100% yield of the olefin. Alternatively, the catalyst may be 48% hydrobromic acid.

Temperatures which can be employed in the oxidation vary quite widely depending upon the reactivity and other characteristics of the other reactants. Temperatures broadly in the range of about −10° to 30 175° C., desirably 25° to 130° C. and preferably 60° to 110° C., can be employed. The reaction is carried out at pressure conditions sufficient to maintain a liquid reaction phase. Although sub-atmospheric pressures can be employed, pressures usually in the range of about atmospheric to somewhat above are most desirable.

The catalysts include compounds of the following: Ti, V, Cr, Se, Zr, Nb, Mo, Te, Ta, W, Re, and U. These may be characterized as forming peracids or as hydroxylation catalysts.

The amount of metal in solution used as catalyst in the process can be varied widely, although as a rule it is desirable to use at least 0.00001 mols and more preferably 0.001 to 0.01 mols per mol of hydroperoxide present. Amounts greater than about 0.1 mols seem to give no advantage over smaller amounts. The catalysts remain dissolved in the reaction mixture throughout the process and can be reused in the reaction after removal of the reaction of 0.01 to 10 mols per mol of the amine, preferably 0.5 to 2.

The catalysts are suitably added as compounds of the above indicated metals; it is possible, however, to add the catalyst as a finely divided metal with the metal being eventually converted to a compound sufficiently soluble to provide a catalytic amount of metal in solution in the reaction mixture. A great number of compounds of titanium, vanadium, chromium, selenium, zirconium, niobium, molybdenum, tellurium, tantalum, tungsten, rhenium, and uranium are suitable for use in carrying out the present invention. Both organic and inorganic compounds can be employed. It is especially advantageous to employ organic compounds which have a relatively high solubility as subsequently described although this is by no means necessary for successful practice of the present invention. Appropriate and illustrative examples of compounds of the catalyst metals which are successfully employed in carrying out the present invention are the oxides, chlorides, oxychlorides, fluorides, phosphates, sulfides and the like of each of the above specified catalyst metals. Heteropolyacids containing the catalyst metal components can be employed. Especially preferred organic compounds are the salts of organic acids such as naphthenates, stearates, octoates and the like. Other preferred compounds are the carbonyl compounds as well as various chelates, association compounds and enol salts. The compounds of all of the above indicated catalyst metals are successfully employed in carrying out the process of this invention.

The molybdenum compounds include the molybdenum organic salts, the oxides such as $Mo_2O_3$, $MoO_2$, molybdic acid, $MoO_3$, the molybdenum chlorides and oxychlorides, molybdenum fluoride, phosphate, sulfide, and the like. Heteropolyacids containing molybdenum can be used as can salts thereof; examples include phosphomolybdic and the sodium and potassium salts thereof. Corresponding or analogous compounds of the other metals mentioned above may be used.

It has been discovered that titanium compounds have unexpected and surprising utility in this reaction. Titanium compounds have been found to be outstandingly effective in the reaction of organic hydroperoxides with amines.

Inorganic as well as organic titanium compounds can be used, although organic compounds give much better results. Preferred titanium compounds are esters or salts of organic acids and are preferably derived from aliphatic or aromatic alcohols and organic acids. Specific examples are tetra n-butyl titanate, di n-butyl di (2, 6 di-t-butyl p-cresyl) titanate, n-butyl trioleoyl titanate, tetra o-cresyl titanate, tetra t-butyl titanate, titanium naphthenate, titanium stearate, titanium ethylhexoate, titanium acetate, and the like. Inorganic compounds such as titanium tetrachloride and the like are useful.

With titanium compounds which hydrolyze readily, it is desirable to remove water of oxidation from the reaction zone during the reaction such as by azeotroping with benzene or the like.

The hydroperoxides used are derived from hydrocarbons. Stable, aralkyl or cycloalkyl hydroperoxides are very useful. Illustrative hydroperoxides can be represented generally by the formula ROOH where R is an aralkyl, aralkenyl, hydroxyaralkyl, hydroxyalkyl, cycloalkyl, cycloalkenyl, hydroxycycloalkyl, alkyl and the like group having about 3 to 20 carbon atoms. Analogous hydroxy-hydroperoxy compounds may be used.

Specific organic hydroperoxides are cyclohexyl hydroperoxide, cyclohex-2-enyl hydroperoxide, t-butyl-hydroperoxide and the hydroperoxides of toluene, ethylbenzene, cumene, p-ethyltoluene, isobutylbenzene, tetralin, diisopropylbenzene, p-isopropyltoluene, o-xylene, m-xylene, p-xylene, phenylcyclohexene, and the like. The preferred species are those derived from cumene, ethylbenzene and isobutane. Mixtures of such hydroperoxides can be used, as may cyclohexanol hydroperoxide, and the like.

For practice of the present invention, catalytic compounds may be employed in the form of a compound or mixture which is initially soluble in the reaction medium. While solubility will, to some extent depend on the particular reaction medium employed, suitably soluble substances contemplated by the invention would include hydrocarbon-soluble, organo-metallic compounds having a solubility in methanol at room temperature of at least 0.1 gram per liter. Illustrative soluble forms of the catalytic materials are the naphthenates, stearates, octoates, carbonyl and the like. Various chelates, association compounds and enol salts, such, for example, as aceto-acetonates may also be used. Specific and preferred catalytic compounds of this type for use in the invention are the naphthenates and carbonyls of molybdenum, vanadium, and tungsten and especially the various titanium compounds.

The oxidation reaction time will vary depending upon the conversion desired. Very short reaction times can be employed where low conversion and/or very active materials are employed. Normally, reaction times from about 10 minutes to 6 hours and desirably from 2 to 24 hours are employed.

The amines used are primary and the amine group may be attached to a primary or secondary saturated carbon atom, and may contain 1 to 20 carbon atoms, preferably 4 to 16 carbon atoms, e.g., benzylamine, isopropylamine, n-butylamine, cyclohexylamine, cyclocctylamine, cyclododecylamine and the like amine substituted saturated aliphatic groups, which may be cyclic or acyclic, which groups may contain cyclic aryl or alkyl substituents.

The concentration of the amine in the reaction mixture may be in the range of 5 to 60% by weight, preferably in the range of 5 to 15%.

The concentration of hydroperoxides in the oxidation reaction mixture at the beginning of the reaction will normally be one percent or more although lesser concentrations will be effective and can be used.

The reaction is suitably carried out in the substantial absence of water. Relatively small amounts of water can be tolerated during the reaction but it is preferable to exclude water from the system during the major part of the reaction.

The process is most advantageously carried out in the presence of a solvent.

A preferred solvent or diluent is t-butanol. However, other alcohols such as t-amyl alcohol, di-methyl propyl carbinol, methyl diethyl carbinol, dimethyl phenyl carbinol and the like may be used. Primary or secondary alcohols may also be used, such as methanol, ethanol, n- or i-propanol, i- or n- or s-butanol as well as analogous pentanols or hexanols. Also, ethers such as diethyl ethers, ketones such as cyclohexanone may be used. The lower aromatic hydrocarbons are suitable solvents as are the lower boiling chlorinated hydrocarbons including chlortoluene.

Where the oxime produced is intended as an intermediate for further synthesis, one may use the crude oxime. If the oxime is to be rearranged, an acid such as sulfuric acid may be mixed with the oxime and heated, in known manner, to convert cyclohexanone oxime to caporlactam.

An important feature of the invention is that cyclohexyl hydroxylamine may be made and this can be further air oxidized to the oxime. Production of this product has the advantage that only 1 mol of hydroperoxide is consumed to make it while 2 mols are needed to produce oxime.

The dehydration catalyst for making styrene may be used in supported form or in pellets. Typical supporting materials are crushed sandstome, silica, filter stone, and ceramically-bonded, fused aluminum oxide. For instance, the support may be wetted with water, titania powder amounting to about 10 to 15 percent of the support then sprinkled on, and the catalyst and support dried at 150° C. The activity of the titania powder may be increased by treating it with hot aqueous sulfuric acid (e.g., 10 percent), followed by thorough washing with water to remove the acid, before the titania is applied to the support. With titania supported on 4 × 6 mesh, ceramically-bonded, fused aluminum oxide, production ratios of 400 to 650 grams of styrene per liter of catalyst per hour may be obtained. Higher production ratios are possible with the titania catalyst in pellet form, e.g., chemically pure anhydrous grade titanium dioxide powder is wetted with water and the resulting paste dried at 130° to 150° C. The dried cake is powdered and then pelleted. The pellets are then fired in a furnace at a temperature of at least 800° C., and they become very strong, mechanically. Then, they may be subjected to an activation step by immersion in boiling aqueous nitric acid (18-20 percent concentration) for a period of about 90 minutes, thorough washing with water, and drying at about 130° to 150° C. Instead of nitric acid, hydrochloric acid, phosphoric acid or sulfuric acid may be used for the acid treatment. At between 800° and 1000° C., there is a shrinkage of the pellet, and the pellets are harder and denser. These denser, harder pellets do not seem to be as readily activated by nitric acid as those roasted at 800° C., even using the concentrated grade of nitric acid. They may be activated however, by aqueous phosphoric acid of 20 percent concentration. With the denser, harder pellet, dusting of the catalyst, e.g., during a charging operation, is largely eliminated, and for this purpose a roasting temperature of about 1000° C. is preferred.

In general, the smaller pellet size the better the production ratio. Pellet sizes measuring less than 3/16 inch in the largest dimension are not practical, mechanically. Good production ratios are obtained with pellets measuring up to ⅜ inch in one or more dimensions.

The desirable temperatures of dehydration are between 180° and 280° C. Usually it is necessary to use temperatures below 220° or above 250° C. At below 220° C. steam or reduced pressure may be employed to assist in vaporizing the carbinol. Temperatures above about 250° to 280° C. may be employed with a high feed rate.

Using cyclohexanol hydroperoxide as the peroxide material in an Example 2 type run gives good results. Another suitable material of this type is iospropanol hydroperoxide. These materials contain an OH group attached to the same carbon as is the OOH group. These may be prepared by starting with the appropriate alcohol instead of the hydrocarbon, as described above. If the alcohol is a by-product of an oxidation step, it may be converted to its hydroperoxide, and then the latter used in an oxidation, giving the corresponding ketone as a side-product These hydroxy-hydroperoxy compounds may be or have been referred to as "ketone hydroperoxides".

Other dehydration methods may be used if desired.

The process may be carried out batchwise, or in an intermittent or continuous manner. As to the latter, the reaction may be carried out in an elongated reaction zone such as a tube or a tower or a plurality of reactors connected in series, and the hydroperoxide may be introduced at spaced points along the path of flow of the solution.

In view of the foregoing disclosures, variations and modifications thereof will be apparent to one skilled in the art, and it is intended to include within the invention all such variations and modifications except as do not come within the scope of the appended claims.

As can be seen from the foregoing working examples, where the production of the hydroxyl amine is desired, the mol ratio of reactants is such that up to about one mol of hydroperoxide is employed per mol of primary amine. Where the essential desired product is the oxime, ratios of reactants of two mols of hydroperoxide per mol of amine or higher are employed. Where the mol ratio of hydroperoxide to amine is between one and two mols of hydroperoxide per mol of amine, mixtures of hydroxyl amine and oxime are produced.

What is claimed is:

1. A process for preparing an oxime and a hydroxylamine from the corresponding primary amine selected from the group consisting of alkyl amines having 3 to 6 carbon atoms, cycloalkyl amines having from 6 to 12 carbon atoms, and benzylamine, the amine group of which is attached to a carbon atom of the class consisting of primary and secondary carbon atoms, which process comprises treating in the substantial absence of water the amine in the presence of a dissolved catalyst which is a compound of titanium, vanadium, chromium, selenium, zirconium, niobium, molybdenum, tellurium, tantalum, tungsten, rhenium and uranium and an organic hydroperoxide as the oxidizing agent.

2. A process for preparing an oxime and a hydroxylamine from the corresponding primary amine selected from the group consisting of alkyl amines having 3 to 6 carbon atoms, cycloalkyl amines having from 6 to 12 carbon atoms, and benzylamine, the amine group of which is attached to a carbon atom of the class consisting of primary and secondary carbon atoms, which process comprises treating in the substantial absence of water the amine in the presence of a dissolved catalyst which is a compound of titanium, vanadium, chromium, selenium, zirconium, niobium, tellurium, tantalum, tungsten, rhenium and uranium and an organic hydroperoxide as the oxidizing agent, said compound being an oxide, an organic salt, an acid, an ester or salt of said acid, or a chloride.

3. A process for preparing an oxime and a hydroxylamine from the corresponding primary amine selected from the group consisting of alkyl amines having from 3 to 6 carbon atoms, cycloalkyl amines having from 6 to 12 carbon atoms, and benzylamine, the amine group of which is attached to a carbon atom of the class consisting of primary and secondary carbon atoms, which process comprises treating in the substantial absence of water the amine in the presence of a dissolved metal compound catalyst selected from the group consisting of Ti naphthenate, V naphthenate, Cr naphthenate, Se naphthenate, Mo naphthenate, Zr naphthenate, Nb naphthenate, W naphthenate, Te naphthenate, Ta naphthenate, Re naphthenate and U naphthenate, permolybdic acid, rhenium heptoxide, tetra n-butyl titanate, di n-butyl di (2,6 di-t-butyl p-cresyl) titanate, n-butyl trioleoyl titanate, tetra-o-cresyl titanate, tetra t-butyl titanate and titanium tetrachloride, and an organic hydroperoxide as the oxidizing agent.

4. The process of preparing cyclohexanone oxime which comprises reacting in the substantial absence of water cyclohexylamine with an organic hydroperoxide at −10° to +175° C. in the presence of Ti naphthenate, V naphthenate, Cr naphthenate, Se naphthenate, Mo naphthenate, Nb naphthenate, W naphthenate, Te naphthenate, Ta naphthenate, Re naphthenate and U naphthenate, permolybdic acid, rhenium heptoxide, tetra n-butyl titanate, di n-butyl di (2,6 di-t-butyl p-cresyl) titanate, and titanium tetrachloride.

* * * * *

UNITED STATES PATENT OFFICE
CERTIFICATE OF CORRECTION

PATENT NO. : 3,960,954
DATED : June 1, 1976
INVENTOR(S) : Joseph Lee Russell, John Kollar It is certified that error appears in the above-identified patent and that said Letters Patent are hereby corrected as shown below:

Col. 4, line 12, change "the" to -- The --

Col. 8, line 9, change " $-10°$ to 30 175°" to -- $-10°$ to $175°$ --

Col. 9, lines 40, 41, change "compounds" to -- components --

Cols. 5 and 6, TABLE 1, first line, shift each of the numbers "1", "2", "3", "4", "5" and "6" one column to the left.

Cols. 5 and 6, TABLE 2, in the line beginning with the word "Benzene", delete "18.3", change "18.0" to -- 18.3 --; change "17.5" to -- 18.0 --; change "18.2" to -- 17.5 --; change "18.4" to -- 18.2 --;
in the column headed "12", insert -- 18.4 -- above "G";
in the column headed "12", change "100" to -- 96 --

Signed and Sealed this

Twenty-sixth Day of April 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 3,960,954            Dated June 1, 1976

Inventor(s) Joseph Lee Russell et al.

It is certified that error appears in the above-identified patent and that said Letters Patent are hereby corrected as shown below:

Column 2, line 60, "as" should read -- and --.

Column 8, line 29, after "reaction" insert the following -- products therefrom. The ratio of the hydroperoxide to the amine is in the range --.

Signed and Sealed this ninth Day of August 1977

[SEAL]

Attest:

RUTH C. MASON
*Attesting Officer*

C. MARSHALL DANN
*Commissioner of Patents and Trademarks*